United States Patent [19]

Miyata et al.

[11] Patent Number: 5,048,952
[45] Date of Patent: Sep. 17, 1991

[54] LIQUID MIXING RATIO SENSOR

[75] Inventors: Shigeru Miyata; Yoshitaka Yamada, both of Nagoya, Japan

[73] Assignee: NGK Spark Plug Co., Ltd., Nagoya, Japan

[21] Appl. No.: 400,450

[22] Filed: Aug. 30, 1989

[30] Foreign Application Priority Data

May 26, 1988 [JP] Japan .................................. 1-133094
Aug. 30, 1988 [JP] Japan ................................ 63-215839

[51] Int. Cl.$^5$ .......................................... G01N 21/41
[52] U.S. Cl. .................................... 356/135; 356/128; 356/136; 250/574; 123/613
[58] Field of Search ............................ 356/128–137; 250/573–574, 577, 227.14; 123/613

[56] References Cited

U.S. PATENT DOCUMENTS

| 3,520,619 | 7/1970 | Ward | 356/130 |
| 3,917,410 | 11/1975 | Ulrich | 356/128 |
| 4,320,291 | 3/1982 | Uramoto | 356/136 |
| 4,843,248 | 6/1989 | Miyata et al. | 250/574 |
| 4,895,444 | 1/1990 | Miyata et al. | 356/128 |
| 4,962,746 | 10/1990 | Miyata et al. | 356/128 |

OTHER PUBLICATIONS

An Optical Probe for Detecting Liquid Interfaces, Instrument Physics Group, Department of Pure and Applied Physics, J. E. Geake, 3–1975.

Primary Examiner—Richard A. Rosenberger
Assistant Examiner—Hoa Pham
Attorney, Agent, or Firm—Cooper & Dunham

[57] ABSTRACT

A liquid mixing ratio detecting sensor has cylindrical holder which is immersed in sulfuric acid solution. The holder is filled with silicone oil. A glass plate is placed within the holder. A light emitting diode emits light beams which enter the glass plate through its vertical side, and totally reflect from a boundary between the glass plate and the sulfuric acid solution. The light beams coming out from the glass plate is reflected by a reflection plate to enter into the glass plate through its vertical side, and totally reflected from a reference boundary between the glass plate and the silicone oil when a refractive index of the sulfuric acid solution is greater than that of silicone oil. On the other hand, the light beams entered into the glass plate refracts at the reference boundary to fall on a photo diode when the refractive index of the sulfuric acid solution decreases to be smaller than that of silicone oil.

6 Claims, 8 Drawing Sheets

PRIOR ART

Fig. 5

PRIOR ART

LIQUID MIXING RATIO SENSOR

BACKGROUND OF THE INVENTION

1. Field of the Invention

This invention relates to a liquid mixing ratio sensor which optically detects mixing ratio of a mixing liquid which includes at least two kinds of liquid components.

2. Description of Prior Art

Electrolyte solution of a battery cell decreases its specific gravity with the development of discharge. The specific gravity and the refraction index are in proportion each other, so that measurement of the refraction index leads to detecting the condition of the battery cell.

These types of sensors have been introduced in Japanese Patent Publication No. 56-37498 and Japanese provisional publication Patent No. 57-84337.

Figure 4:
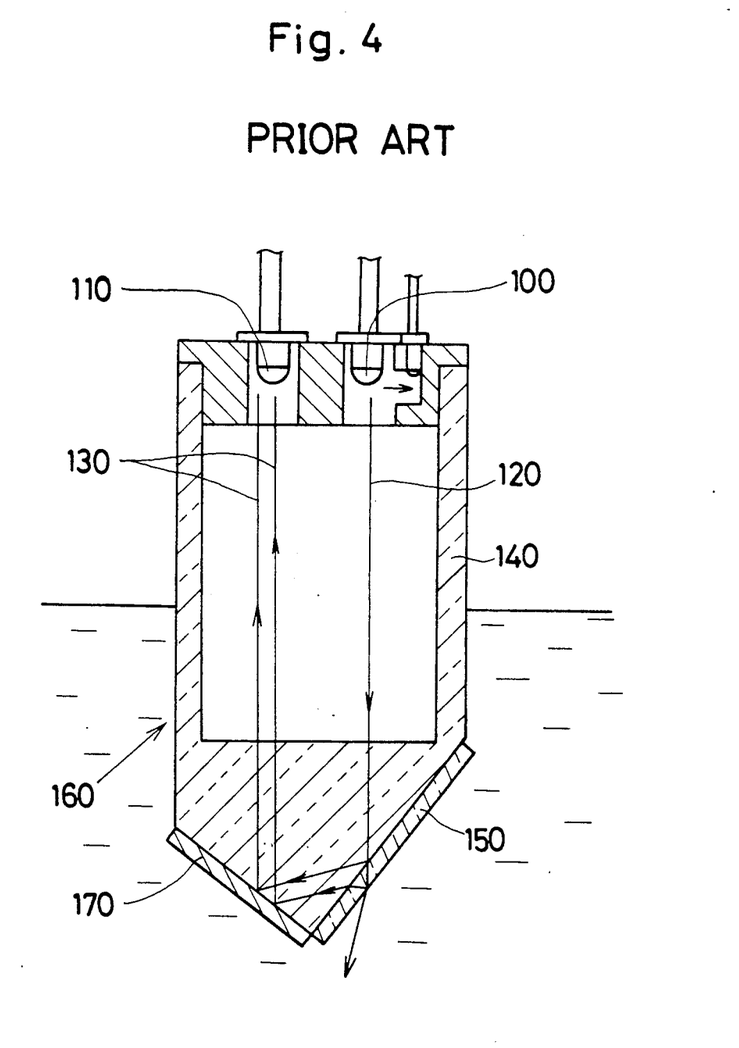
FIGS. 4 and 5 are views showing prior art sensors.

In the Japanese Patent Publication No. 56-37498, a sensor is provided which has a light source 100, a light sensitive element 110 and a light reflection mirror 170 as seen in FIG. 4. Incident light beams 120 and reflection light beams 130 have incident angle toward an optical axis.

The incident angle is determined to be less than a light critical angle which is formed from a transparent material 160 consisting a glass 150 and a transparent synthetic material 140 toward a liquid.

Figure 5:
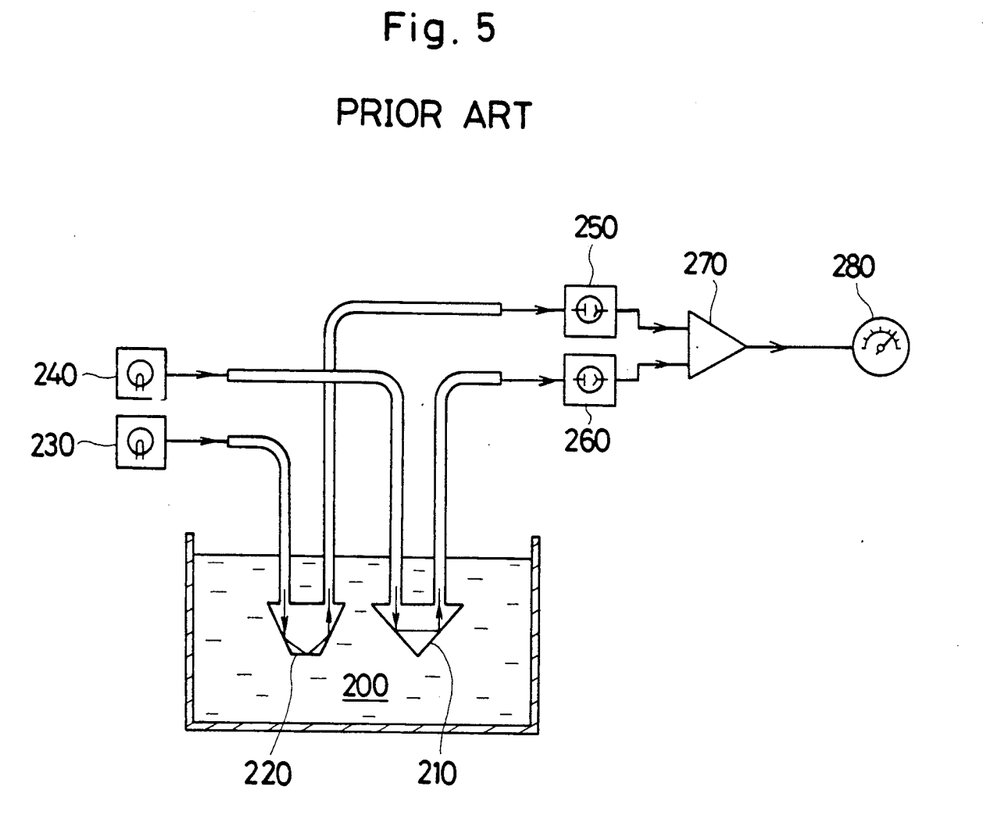

In the Japanese provisional publication Patent No. 57-84337, there are provided a sensor comprising a triangular prism 210, a trapezoid prism 220 disposed in the liquid to be detected, first light source 230, second light source 240, first optoelectronic transducer 250 and second optoelectronic transducer 260, a calculator 270 which is electrically connected to the first and second transducers 250, 260 and a displa device 280a as seen in FIG. 5.

However, the transparent material of the former has $-1 \times 10^{-6}/°$ C. at its thermal coefficient of refraction index, while thermal coefficient of refraction index of the mixing liquid to be detected is $-2 \times 10^{-4}/°$ C. $\sim -6 \times 10^{-4}/°$ C. Change of the ambient temperature causes to variation of the critical angle so as to produce error in measurement values.

The latter has two prisms which makes all the structure great in dimension, and required to do complicated calculations to compensate for temperature.

Therefore, the invention has its object to provide a mixing liquid ratio sensor which is capable of eliminating all the drawbacks mentioned above, enabling to provide a mixing liquid ratio sensor which detects mixing ratio with high precision, low cost and simple construction.

According to the invention there is provided a liquid mixing ratio sensor which includes a boundary in which a transparent plate contacts at one end with a mixing liquid of at least two kinds of liquid components, and having a light emitting element, a light receiving element which detects a mixing ratio of the mixing liquid by a change of light reflection from the boundary;

the sensor comprising;

the transparent plate making other end contact with a gel-like transparent material to serve as a reference boundary, a refraction index of the gel-like transparent material being identical to that of the mixing liquid at desired the mixing ratio to be detected;

the light emitting element having a reflection side, and the light emitting element and the reflection side being located to oppose to a wall perpendicular to both ends of the transparent material, the reflection side being placed such as to reflect light beams reflected from the boundary toward the reference boundary;

a light screen placed at the transparent plate to prevent the light beams from entering the reflection side, the light beams being ones which does not reflect from the boundary;

the light receiving element being located such that the light beams from the light emitting element reflects from the boundary, the reflection side, and refracted at the reference plate to fall on the light receiving element when the refraction index of the mixing liquid to be detected is less than that of the gel-like transparent material.

These and other objects and advantages of the invention will be apparent upon reference to the following specification, attendant claims, and drawings.

DETAILED DESCRIPTION OF THE INVENTION

Figure 1:
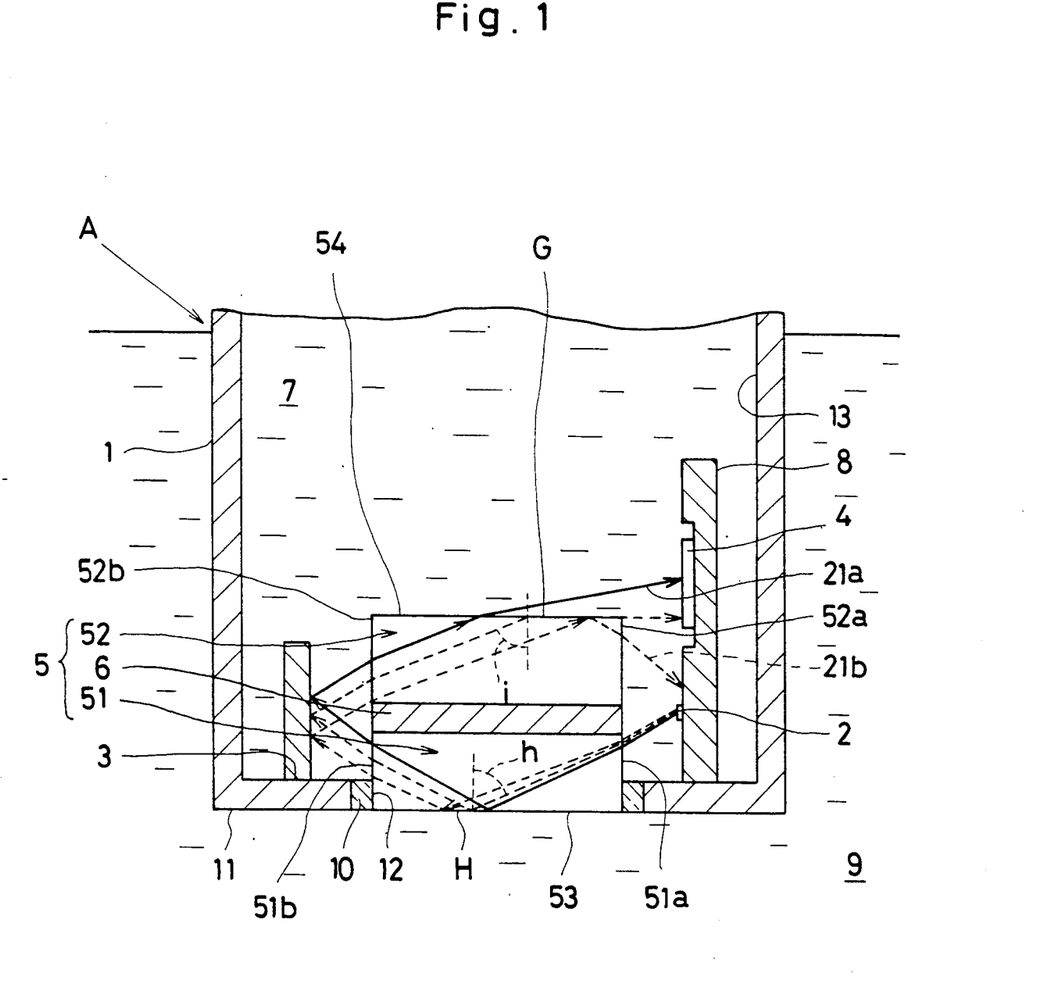
FIG. 1 is a cross sectional view of a sensor according to first embodiment of the invention.

Referring to FIG. 1 in which a sensor (A) incorporated into a sensor which is adapted to detect charging condition of a battery cell, the sensor (A) has a cylindrical holder 1 (4 mm in diameter), a light emitting element 2 (light emitting diode), a reflection plate 3, a light receiving element 4 (photo diode) and a light screen 6. A transparent plate 5 is provided to interpose the light screen 6. Into the holder 1, silicone oil 7 (transparent material) is encapsulated. The holder 1 has a hole 12 at an end 11 which is brought into engagement with a mixing liquid 9 (sulfuric acid solution) to be detected. The transparent plate 5 comprising a lower glass disc 51 and an upper glass disc 52, each of which is made of lead glass (1.64 in refraction index). Between the lower glass disc 51 and the upper glass disc 52, the light screen 6 is interposed. The lower glass disc 51 engages at its lower end 53 with the sulfuric acid solution 9 to form a boundary (H). The upper glass disc 52 engages at its upper end 54 with the silicone oil 7 to form a reference boundary (G). Both upper and lower ends 54, 53 are in parallel relationship each other. The transparent plate 5 exposures the end 53 from the hole 12, and fixed by means of a glass sealant 10 which maintains liquid-tightness of the silicone oil 7. An annular space is formed between the side 55 perpendicular to the end 53 and an inner side 13 of the holder 1. Into the annular space, the light emitting diode 2 and the photo diode 4 which are attached to a base 8, are placed in opposed relationship with the reflection plate 3. Residual space of the holder 1 is filled with the transparent material 7 (silicone oil). The light emitting diode 2 is located to oppose to the light screen 6 such that light beams not reflected from the boundary (H) is prevented from entering the reflection plate 3. The photo diode 4 is located at the base 8 which corresponds to the above of the upper glass disc 52, and opposing to the light beams emitted from the light emitting diode 2, reflected from the boundary (H) and the reflection plate 3, and refracted at the reference boundary (G) to come out. The reflection plate 3 and the photo diode 4 are located in perpendicular to the boundary (H) and the reference boundary (G). The refraction index (1.34) of the transparent material (silicone oil) 7 is determined to be equal to that of the sulfuric acid solution 9 to be detected when the battery cell is discharged. The light emitting diode 2 is of gallium arsenic (GaAs) type which is adapted to emit infrared rays 21.

The infrared light beams emitted from the light emitting diode 2 enters the silicone oil 7 and invades into the lower glass disc 51, further proceeding through the lower glass disc 51 to reflect from the boundary (H), and proceeding the lower glass disc 51 and the silicone oil 7 after reflecting from the reflection plate 3 to invade into the upper glass disc 52 to be incident on the reference boundary (G) between the upper glass disc 52 and the silicone oil 7.

In this instance, the light beams 21b which has a critical angle of more than an angle (i), totally reflects at the reference boundary (G).

On the other hand, the light beams 21a which has a critical angle of less than the angle (i), totally refracts at the reference boundary (G).

When the battery cell has discharged with refraction index of the sulfuric acid solution 9 smaller than that of the silicone oil 7 (1.34), a critical angle (h) at the boundary (H) becomes small.

Among the infrared rays, there are rays 21a having an incident angle smaller than the critical angle (i), the rays 21a refracts at the reference boundary (G) to fall on the photo diode 4. The amount of light beams incident on the photo diode 4, increases with the decrease of the refraction index of the sulfuric acid solution 9. This hold true when the sulfuric acid solution 9 is evaporated to decrease its quantity.

When the battery cell is fully charged with refraction index of the sulfuric acid solution 9 greater than that of the silicone oil 7 (1.34), the critical angle (h) at the boundary (H) becomes greater. The incident angle of the infrared rays 21 incident on the reference boundary (G) becomes greater than the critical angle (i) reflected from the boundary (G), and the rays 21 totally reflects, so that there is no rays incident on the photo diode 4.

Figure 2:
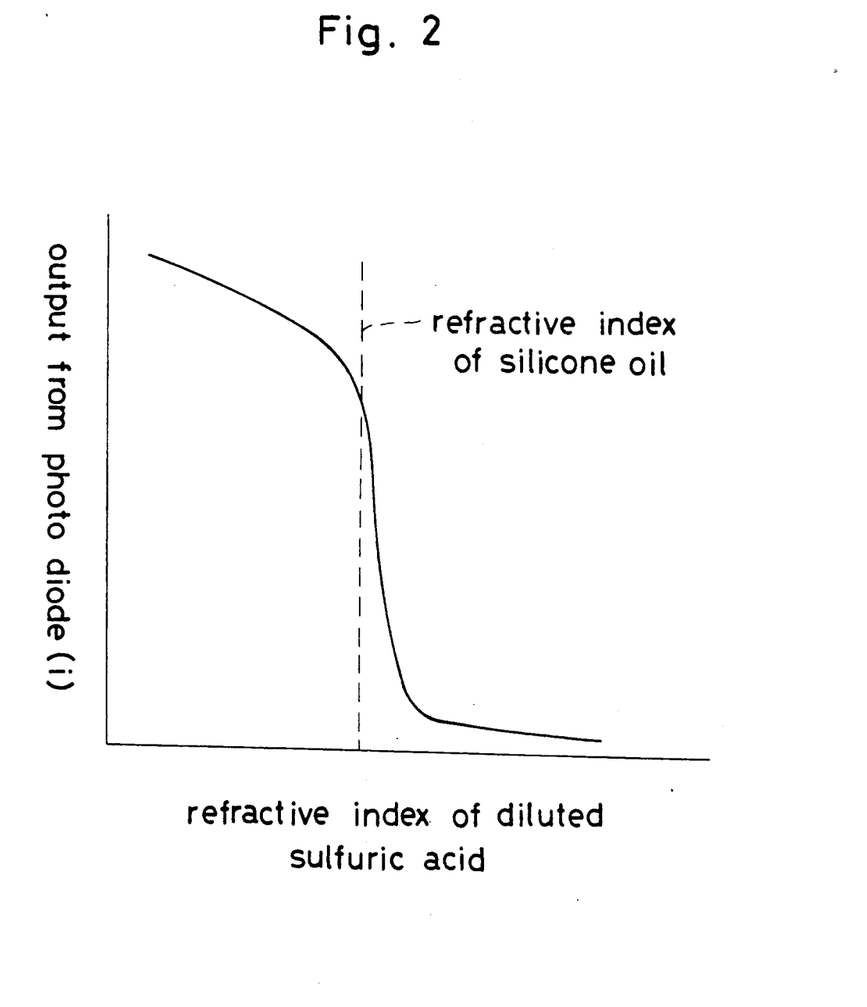
FIG. 2 is a graph showing relationship between refraction index of a transparent material and that of a liquid to be detected.

FIG. 2 is a graph showing relationship between output from the photo diode 4 and the refraction index of the sulfuric acid solution 9.

The sensor (A) according to the first embodiment of the invention, the following advantages are obtained.

The amount of the sulfuric acid solution 9 and the electric current are measured on the base of optical critical angle. This enables to continuously monitor the amount with the battery cell in operation.

The refraction index of the sulfuric acid solution 9 is subjected to change depending on the ambient temperature. The temperature of the silicone oil 7 is subjected to change so as to change the refraction index. The incident angle of the infrared rays 21 is restricted to be smaller than the critical angle determined by the sulfuric acid solution 9 and the lower glass disc 51.

Therefore, it enables to decrease the error in reference to the temperature.

Elimination of the temperature compensation device makes it possible to readily manufacture the sensor (A) with low cost and simple construction.

A modification form of the first embodiment are described below.

In this modified form, the upper glass disc 52 and the lower glass disc 51 are made of transparent glass of different refraction index.

The selection of the transparent glass is such that the critical angle determined by refraction index of the lower glass disc 51 and that of the sulfuric acid solution 9, is equal to the critical angle determined by the refraction index of the upper glass disc 52 and that of the transparent material.

According to the modification form, it is easily found that the freedom of selection regarding to the mixing liquid to be detected increases to a significant degree.

Figure 3:
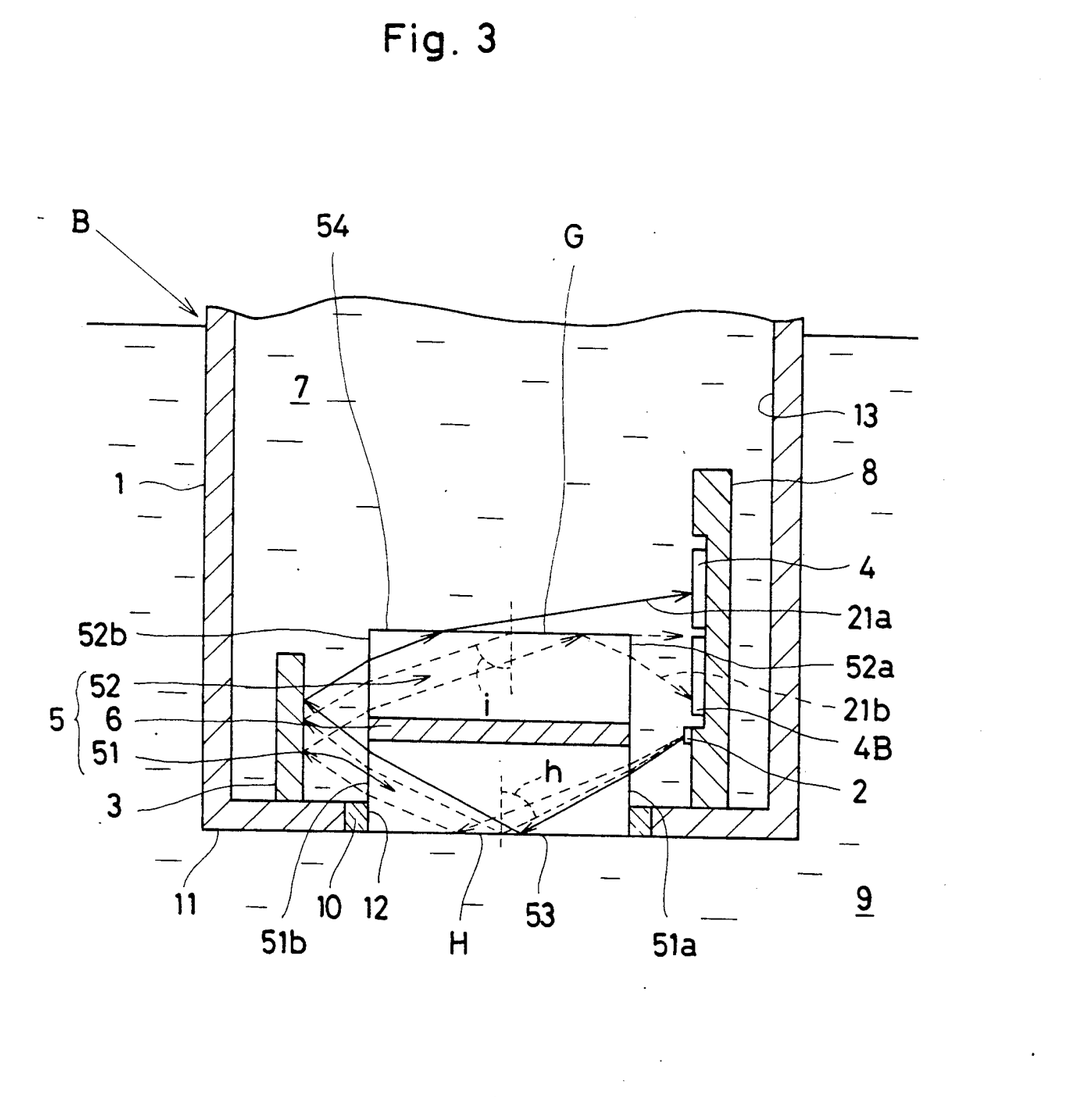
FIG. 3 is a cross-sectional view of the sensor according to second embodiment of the invention.

Referring to FIG. 3, second embodiment of the invention is described as below.

A sensor (B) according to the second embodiment is similar to the sensor (A) except addition of second photo diode (4B). In FIG. 3, like numerals similar to those of FIG. 1 are designated as identical numerals throughout the drawings.

The photo diode 4 is located at the base 8 which corresponds to the above of the upper glass disc 52, in a same manner as mentioned in the first embodiment of the invention, and opposing to the light beams emitted from the light emitting diode 2, reflected from the boundary (H) and the reflection plate 3, and refracted at the reference boundary (G) to come out.

The reflection plate 3 and the photo diode 4 are located in perpendicular to the boundary (H) and the reference boundary (G). The refraction index (1.34) of the transparent material (silicone oil) 7 is determined to be equal to that of the sulfuric acid solution 9 to be detected when the battery cell is discharged. The light emitting diode 2 is of gallium arsenic type which is adapted to emit infrared rays 21.

The infrared light beams emitted from the light emitting diode 2 enters the silicone oil 7 and invades into the lower glass disc 51, further proceeding through the lower glass disc 51 to reflect form the boundary (H), and proceeding the lower glass disc 51 and the silicone oil 7 to invade into the upper glass disc 52 to be incident on the reference boundary (G) between the upper glass disc 52 and the silicone oil 7.

In this instance, the light beams 21b which has a critical angle of more than the angle (i), totally reflects at the reference boundary (G).

On the other hand, the light beams 21a which has a critical angle of less than the angle (i), totally refracts at the reference boundary (G).

When the battery cell has discharged with refraction index of the sulfuric acid solution 9 smaller than that of the silicone oil 7 (1.34), the critical angle (h) at the boundary (H) becomes small.

Among the infrared rays, there are rays 21a having an incident angle smaller than the critical angle (i), the rays 21a refracts at the reference boundary (G) to fall on the photo diode 4. The amount of light beams incident on the photo diode 4, increases with the decrease of the refraction index of the sulfuric acid solution 9. This hold true when the sulfuric acid solution 9 is evaporated to decrease its quantity.

When the battery cell is fully charged with refraction index of the sulfuric acid solution 9 greater than that of the silicone oil 7 (1.34), the critical angle (h) at the boundary (H) becomes greater. The incident angle of the infrared rays 21 incident on the reference boundary (G) becomes greater than the critical angle (i) reflected from the boundary (G), and the rays 21 totally reflects, so that there is no rays incident on the photo diode 4.

In this instance, there is the light beams 21b incident on the second photo diode 4B.

The sensor (B) according to the second embodiment of the invention, the following advantages are obtained.

The differential of the refraction index is found by comparing out of the photo diode to that of the second photo diode 4B.

This enables to maintain high measurement precision even though the light emitting diode 2, the photo diode 4 and the second photo diode 4B have respectively deteriorated to lose their good efficiency.

This enables to maintain relatively stable measurement value even when ambient light beams due to diffused reflection falls on the second photo diode 4B.

It is appreciated that the mixing liquid to be detected may be of mobile or stationary type.

Further, it is noted that a transparent plate may be of property which resists erosion of the mixing liquid to be detected such as sodium glass, Pyrex glass, borosilicate glass or acryl synthetic resin.

Furthermore, it is noted that the transparent plate may be of polygon or ellipse as long as the transparent plate has one side opposed to the photo and light emitting diode being parallel to other side opposed to the reflection plate.

Figure 6:
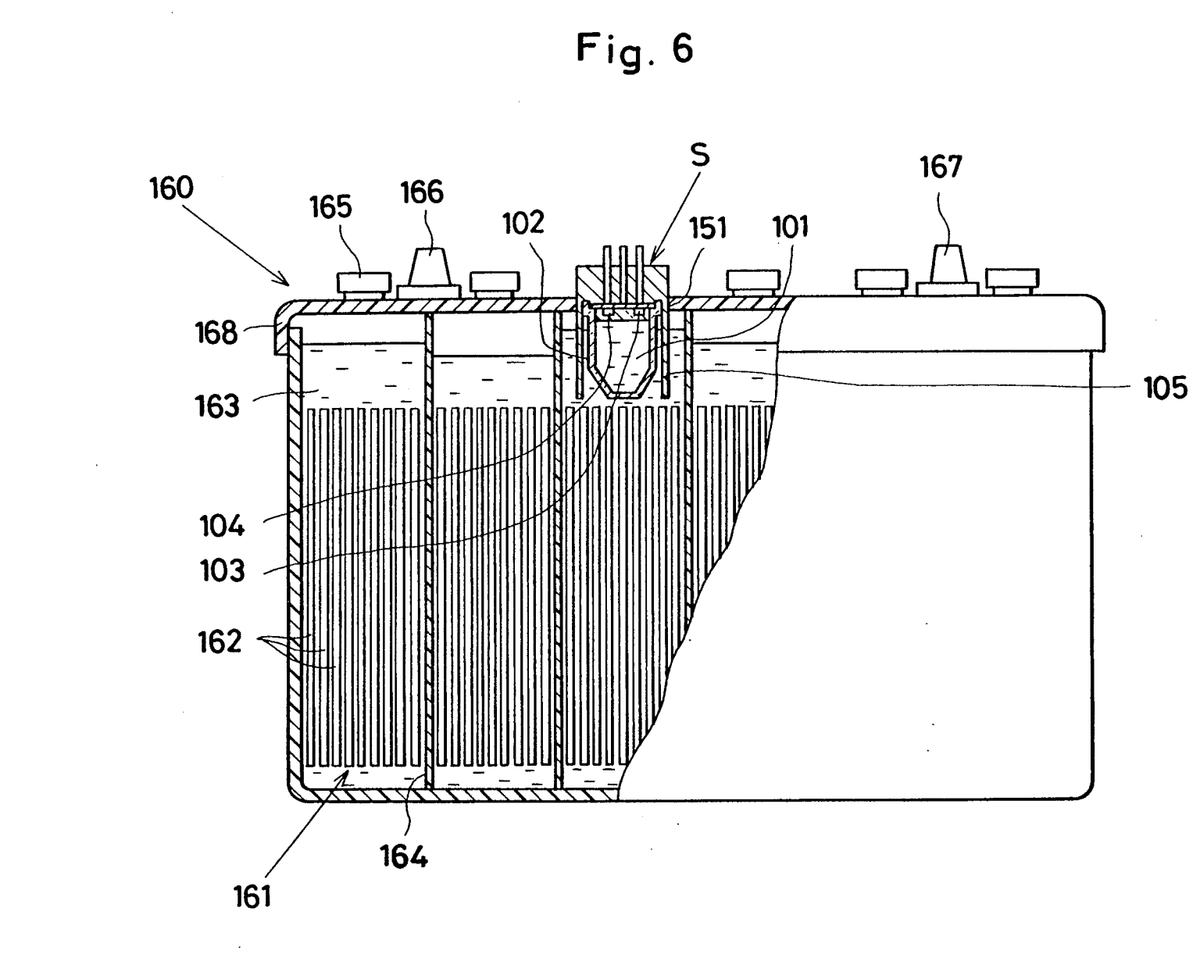
FIG. 6 is a schematic view of a sensor incorporated into a battery cell, but partly broken away.
Figure 7:
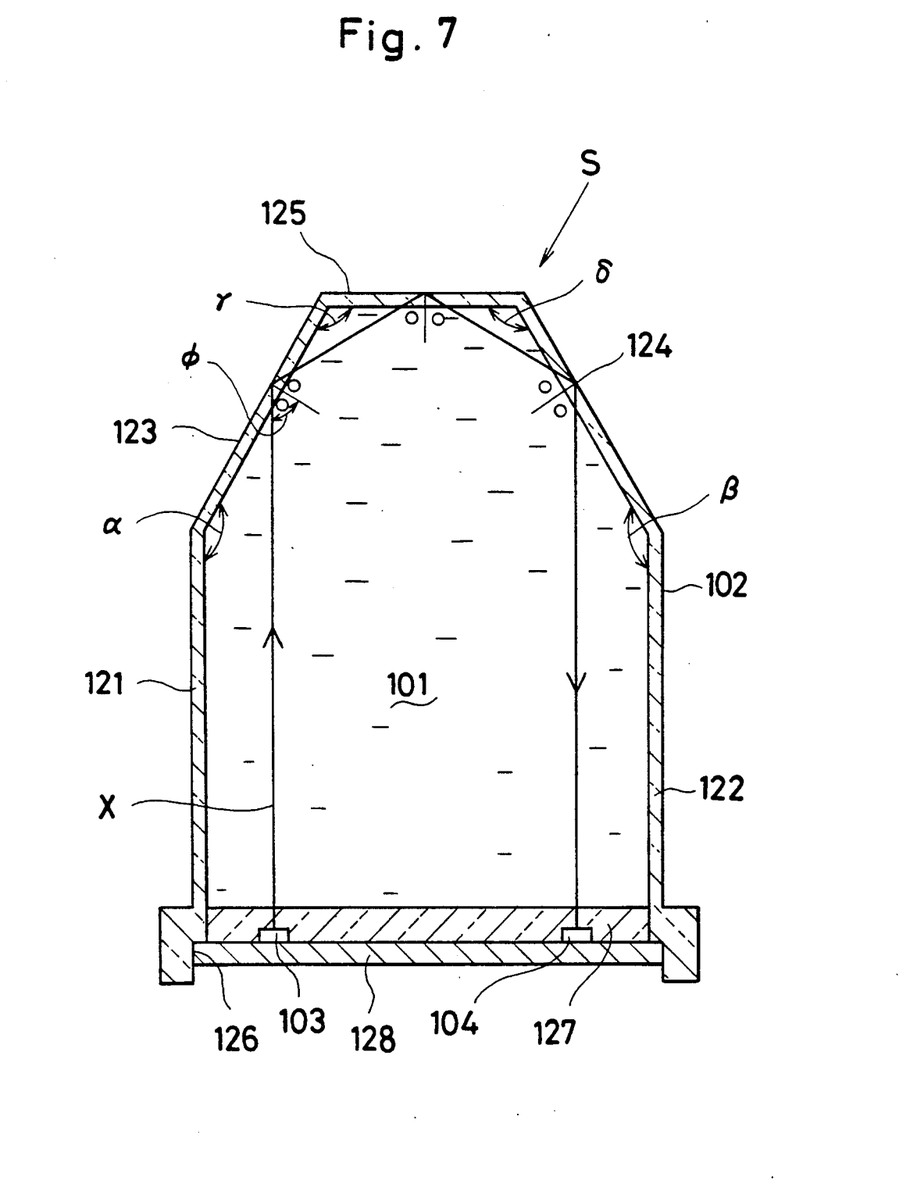
FIG. 7 is a cross sectional view showing optical path when diluted sulfuric acid solution in a battery cell decreases at its concentration below the predetermined concentration level.
Figure 8:
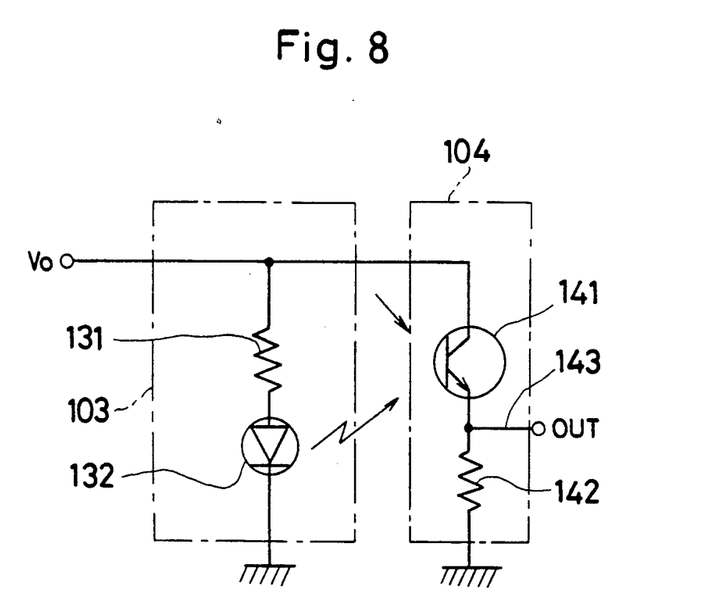
FIG. 8 is an wiring diagram of a sensor according third embodiment of this invention.

Now, third embodiment of the invention is described in reference to FIGS. 6, 7 and 8 in which a sensor is incorporated into discharge detector (S).

The detector (S) has a transparent casing 102 filled with silicone oil 101, a light emitting element 103, a photo diode 104 (light receiving element) and a light screen pipe 105. The detector (S) is fixed to a cell 161 of a battery cell 160.

The silicone oil 101 has refraction index of 1.575. The transparent casing 102 has parallel-opposed side walls 121,122, slant walls 123, 124 and a bottom base 125, each of which is made of epoxy resin having a refraction index of 1.575.

The side wall 121 and the slant wall 123 form an angle ($\alpha$) of 150 degrees.

On the other hand, the side wall 122 and the slant wall 124 form an angle ($\beta$) of 150 degrees. Angle ($\gamma$) formed between the slant wall 123 and the bottom base 125 is 120 degrees. Angle ($\delta$) formed between the slant wall 124 and the bottom base 125 is 120 degrees. The casing 102 has a opening 126 by the side walls 121, 122 in opposed relationship with the bottom base 125. The opening 126 is coved by a light screen 128, while the light emitting element 103 and the light receiving element 104 are embedded at a bonded portion between the epoxy resin 127 and the light screen 128. The light emitting element 103 is adapted to light a GaAs type light emitting diode 132 when a voltage (Vo) is applied across the light emitting diode 132 by way of a resistor 131 as seen in FIG. 8. The light receiving element 104 has NPN type photo diode 141, and outputs through an output terminal 143 connection between emitter of the photo diode 141 and a resistor 142 in accordance with the intensity of light beams received.

The photo diode 141 is located such as to received the light beams (X) which totally reflected from the slant walls 123, 124 and the bottom base 125.

In this instance, the light beams (X) formed with the slant walls 123, 124 and the bottom base 125 is of an incident angle ($\phi$) of 60 degrees. It is noted that the output terminal is connected to a control circuit (not shown).

Outside the casing 102, the light screen pipe 105 is provided to prevent the ambient light from entering the photo diode 141, and fixed by a thread cut on a surface of the pipe 105.

The battery cell 160 has positive and negative electrode plate 162, and containing an electrolyte solution 163 which has a refraction index of circa 1.364 when fully discharged.

The cell 161 is of upper open end type, six of which are connected in series at a partition 64, and having a lid 168 which is provided with a plug 165, negative and positive terminals 167, 166.

The detector (S) is placed into third cell 161 from the positive terminal 166 by means of a screw 151. The slant walls 123, 124 are adapted to immerse into the electrolyte solution at lower level.

In this instance, the light beams from a light emitting diode 132 (photo diode) is adapted to totally reflect at a critical angle of 60 degrees when the sulfuric acid solution 163 in the battery cell 160 decreased its concentration to a lower limit with the refraction index of the acid solution 163 as 1.575.

In operation, when concentration of the sulfuric acid solution 163 is high enough with the refraction index of the acid solution 163 more than 1.364, the light beams (X) pass through the slant walls 123, 124 and the bottom base 125 when the incident angle ($\phi$) on the slant walls 123, 124 and the bottom base 125 is 60 degrees. In this instance, the photo diode 141 receives no light beams from the photo diode 132 so as to produce no output.

On the outer hand, when concentration of the sulfuric acid solution 163 is insufficient with the refraction index of the acid solution 163 in less than 1.364, the light beams (X) respectively reflect at the slant walls 123, 124 and the bottom base 125 when the incident angle ($\phi$) on the slant walls 123, 124 and the bottom base 125 is 60 degrees.

In this instance, the photo diode 141 receives the light beams from the photo diode 132 so as to generate output in accordance with the light beams received.

When the angles ($\alpha$), and ($\beta$) become 149 degrees in turn, While the angle ($\gamma$) and ($\delta$) become 121 degrees in turn due to dimension a error at the time of moulding the transparent casing 2, the incident angle ($\phi$) becomes 59 degrees which is lower than 60 degrees determined as a critical angle. This shows that the total reflection does not occur until the refraction index of the sulfuric acid 163 decreases in less than 1.350.

As a result, it is impossible to detect the discharged state of the battery cell 160 until the concentration of the sulfuric acid solution 163 decreases to less than previously aimed concentration.

However, by supplying the silicone oil 101 having refraction index of 1.591, the incident angle from the casing 102 to the sulfuric acid solution 163 becomes 60 degrees when the angle ($\phi$) is 59 degrees which serves as a critical angle toward the sulfuric acid solution 163.

Therefore, it becomes possible to detect the discharge state of the battery cell 160 when the refraction index of the sulfuric acid solution 163 decreases in less than 1.364.

As understood from the structure thus far described, change of the refraction index of the silicone oil 101 makes it posssible to compensate the dimensional error at the time of moulding the casing 102.

This holds true when dimesional error occurs on the distance between the photo diode 141 and the light emitting diode 132.

It is noted that the sensor according to the present invention may be applied when detecting concentration of electrolyte solution other than that of the sulfuric acid solution 163.

Further, the sensor according to the present invention may be applied when detecting concentration of organic component solution.

While the invention has been described with reference to the specific embodiment, it is understood that this description is not to be construed in a limiting sense in as much as various modifications and additions to the specific embodiment may be made by skilled artisan without departing from the spirit and scope of the invention.

What is claimed is:

1. A liquid mixing ratio detecting sensor comprising:
   a hollow cylindrical holder which is adapted to be immersed in a liquid solution;
   a transparent material placed within an inner space of the holder to serve as a reference;
   a transparent plate placed within the holder, the upper end of the plate being brought in contact with the transparent material to form a reference boundary between the transparent material and the transparent plate, the lower end of the transparent plate being brought in contact with the liquid solution to form a boundary between the transparent plate and the liquid solution;
   a light emitting element located to face one vertical side, so that light beams emitted from the element enter into the transparent plate through its vertical side, and totally reflected from the boundary to come out from the transparent plate through the other vertical side of the plate;
   a reflection plate placed within the holder to interpose the transparent plate with the light emitting element, and reflecting the light beams coming out of the other vertical side of the transparent plate to make the light beams enter into the transparent plate through the vertical side, and making the light beams totally reflect from the reference boundary, when the refractive index of the liquid solution is greater than that of the transparent material;
   a light receiving element located above the light emitting element to receive the light beams refracted from the reference boundary to generate an output in accordance with the light beams received, when the refractive index of the liquid solution decreases to be smaller than that of the transparent material.

2. In a liquid mixing ratio detecting sensor as recited in claim 1, a second light receiving element is provided between the light emitting element and the light receiving element so as to received light beams totally reflected from the reference boundary, and comparing the output generated by the light receiving element and the output generated by the second light receiving element.

3. In a liquid mixing ratio detecting sensor as recited in claim 1, the transparent plate is divided into upper and lower half pieces of different refractive indices by means of a light screen which prevent the light beams from the light emitting element from directly entering the reflection plate through the transparent plate, the refractive indices of the lower and upper half pieces being such that the critical angle determined by the upper half piece and the transparent material is adapted to be equal to that determined by the lower half piece and the liquid solution when the difference the between the refractive index of the transparent material and that of the liquid solution is great.

4. A liquid mixing ratio detecting sensor comprising;
   a hollow transparent casing having parallel, opposed side walls, slant walls and a bottom base, one slant wall continuously connecting one side wall to the bottom base while the other slant wall continuously connects the other side wall to the bottom base;
   the transparent casing being immerse in liquid solution, with the inner space of the transparent casing being filled with a reference transparent material;
   a light emitting element placed at the transparent casing to emit light beams toward the one slant wall of the casing through the transparent material, and the light beams refracted at the one slant wall when the refractive index of the liquid solution is greater than that of the transparent material;
   a light receiving element placed at the transparent casing to receive the light beams totally reflected from the one side wall, the bottom base and the other side wall, respectively, when the refractive index of the liquid solution is smaller than that of the transparent material;
   the transparent material being chosen with one which has a greater refractive index to compensate for dimensional errors which decrease the angle between the side wall and the slant wall of the transparent casing.

5. In a liquid mixing ratio detecting sensor as recited in claim 4 the liquid solution is dilute sulfuric acid having a refractive index of more than 1,364, while the transparent material is silicone oil having a refractive index of 1.340.

6. In a liquid mixing ratio detecting sensor as recited in claim 5, the transparent casing has an angle of 150 degrees between the side wall and the slant wall and at the same time having an angle of 120 degrees between the slant wall and the bottom base, when the angle between the side wall and slant wall being changed to 149 degrees by the dimensional errors, the silicone oil is replaced with one which has a refractive index of 1.591.

* * * * *